(12) United States Patent  
Kulkarni et al.

(10) Patent No.: US 8,265,766 B1
(45) Date of Patent: Sep. 11, 2012

(54) METHODS AND SYSTEMS OF AUTOMATICALLY DETECTING AN IMPEDANCE OF ONE OR MORE ELECTRODES IN A COCHLEAR IMPLANT SYSTEM

(75) Inventors: Abhijit Kulkarni, Newbury Park, CA (US); Lakshmi N. Mishra, Valencia, CA (US); Leonid M. Litvak, Los Angeles, CA (US); Mark B. Downing, Valenica, CA (US); Aniket Saoji, Northridge, CA (US); Patrick T. Wong, Torrance, CA (US)

(73) Assignee: Advanced Bionics, LLC, Valencia, CA (US)

( * ) Notice: Subject to any disclaimer, the term of this patent is extended or adjusted under 35 U.S.C. 154(b) by 920 days.

(21) Appl. No.: 12/342,859

(22) Filed: Dec. 23, 2008

(51) Int. Cl.
 *A61N 1/36* (2006.01)
 *A61N 1/18* (2006.01)
(52) U.S. Cl. .................. 607/56; 607/55; 607/57
(58) Field of Classification Search .......... 607/55, 607/56, 57; 606/129
 See application file for complete search history.

(56) References Cited

U.S. PATENT DOCUMENTS

| | | | |
|---|---|---|---|
| 4,400,590 A | 8/1983 | Michelson | |
| 4,532,930 A | 8/1985 | Crosby et al. | |
| 4,592,359 A | 6/1986 | Galbraith | |
| 4,947,844 A | 8/1990 | McDermott | |
| 5,522,865 A * | 6/1996 | Schulman et al. | 607/56 |
| 5,824,022 A | 10/1998 | Zilberman et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 7,107,101 B1 * | 9/2006 | Faltys | 607/55 |
| 2009/0125081 A1 * | 5/2009 | Spitzer et al. | 607/55 |

* cited by examiner

*Primary Examiner* — Carl H. Layno
*Assistant Examiner* — Jon-Eric C. Morales
(74) *Attorney, Agent, or Firm* — AdvantEdge Law Group, LLC (57) ABSTRACT

Methods and systems for automatically detecting an impedance of one or more electrodes in a cochlear implant system include providing an implantable cochlear stimulator coupled to one or more electrodes, generating an electrical stimulation current with the implantable cochlear stimulator in accordance with stimulation parameters, automatically detecting an impedance of at least one of the electrodes in accordance with a predefined schedule, and performing a predefined action in accordance with the detected impedance.

20 Claims, 8 Drawing Sheets

METHODS AND SYSTEMS OF AUTOMATICALLY DETECTING AN IMPEDANCE OF ONE OR MORE ELECTRODES IN A COCHLEAR IMPLANT SYSTEM

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems generally employ an array of electrodes that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. These are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

Each electrode implanted within a cochlea has a certain impedance associated therewith. These impedance values are often used to determine one or more stimulation parameters during an initial fitting session to fit a cochlear implant system to a patient. However, electrode impedances may change over time, thus resulting in decreased sound quality, distorted pitch, and/or system malfunction.

SUMMARY

Methods of automatically detecting an impedance of one or more electrodes in a cochlear implant system include providing an implantable cochlear stimulator coupled to one or more electrodes, generating an electrical stimulation current with the implantable cochlear stimulator in accordance with one or more stimulation parameters, automatically detecting an impedance of at least one of the electrodes in accordance with a predefined schedule, and performing a predefined action in accordance with the detected impedance.

Systems for detecting an impedance of one or more electrodes in a cochlear implant system include an implantable cochlear stimulator, one or more electrodes electrically coupled to the implantable cochlear stimulator, and a sound processing unit. The sound processing unit is configured to direct the implantable cochlear stimulator to apply a stimulation current to a stimulation site within a patient via at least one of the electrodes, automatically detect an impedance of at least one of the electrodes in accordance with a predefined schedule, and perform a predefined action in accordance with the detected impedance.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

DETAILED DESCRIPTION

Methods and systems of automatically detecting an impedance of one or more electrodes in a cochlear implant system are described herein. In some examples an implantable cochlear stimulator, one or more electrodes electrically coupled to the implantable cochlear stimulator, and a sound processing unit are provided. The sound processing unit may be configured to direct the implantable cochlear stimulator to apply a stimulation current to a stimulation site within a patient via at least one of the electrodes, automatically detect an impedance of at least one of the electrodes in accordance with a predefined schedule, and perform a predefined action in accordance with the detected impedance. In this manner, suboptimal performance of the cochlear implant system related to a change in impedance may be diagnosed and remedied.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment.

The appearance of the phrase "in one embodiment" in various places in the specification are not necessarily all referring to the same embodiment.

To facilitate an understanding of the methods and systems described herein, an exemplary cochlear implant system 100 will now be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; 5,824,022; 6,219,580; 6,272,382; and 6,308,101. All of these listed patents are incorporated herein by reference in their respective entireties.

Figure 1:
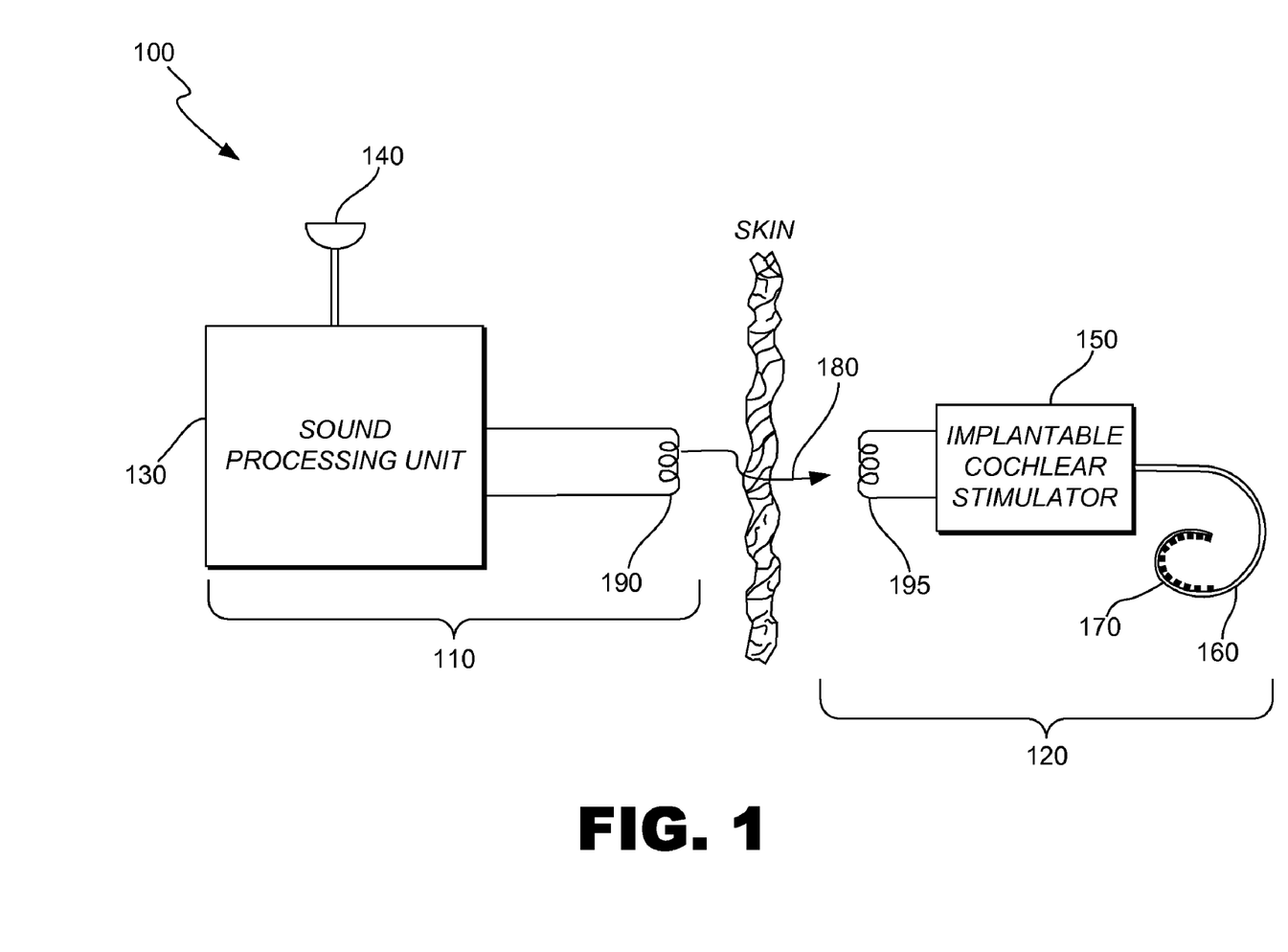
FIG. 1 illustrates an exemplary cochlear implant system according to principles described herein.

As shown in FIG. 1, the cochlear implant system 100, also referred to herein as a cochlear prosthesis, includes an external sound processor portion 110 and an implanted cochlear stimulation portion 120. The sound processor portion 110 may include a sound processing unit 130, a microphone 140, and/or additional circuitry as best serves a particular application. The cochlear stimulation portion 120 may include an implantable cochlear stimulator (ICS) 150, a lead 160 with an array of electrodes 170 disposed thereon, and/or additional circuitry as best serves a particular application. It will be recognized that the sound processor portion 110 may alternatively be located internal to the patient.

The microphone 140 of FIG. 1 is configured to sense acoustic signals and convert the sensed signals to corresponding electrical signals. The electrical signals are sent to the sound processing unit 130 over an electrical or other suitable link. Alternatively, the microphone 140 may be connected directly to, or integrated with, the sound processing unit 130.

The sound processing unit 130 may include any combination of hardware, software, and/or firmware as best serves a particular application. For example, the sound processing unit 130 may include one or more processors, digital signal processors (DSPs), filters, memory units, etc. In some examples, as will be described in more detail below, the sound processing unit 130 may include one or more alert facilities (not shown) configured to convey one or more alerts or other communications to a patient.

In some examples, the sound processing unit 130 may be configured to process the converted acoustic signals in accordance with a selected sound processing strategy to generate appropriate control signals or stimulation parameters for controlling the ICS 150. The electrical stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, ramp on time, and ramp off time of the stimulation current that is applied to the stimulation site.

It will be recognized that the sound processing unit 130 shown in FIG. 1 is merely illustrative of the many different sound processing units that may be used in connection with the present systems and methods. For example, the sound processing unit 130 may include a behind-the-ear (BTE) unit configured to be positioned behind the ear. Alternatively, the sound processing unit 130 may include a portable speech processor (PSP) device, a conventional hearing aid, or any other type of sound processing unit. In certain examples, the sound processing unit 130 may be removed from behind the ear or other operating location by the patient prior to sleeping and replaced upon waking.

The lead 160 of FIG. 1 is adapted to be inserted within a duct of a patient's cochlea. As shown in FIG. 1, the lead 160 includes an array of electrodes 170 disposed along its length. It will be recognized that any number of electrodes 170 may be disposed along the lead 160 as may serve a particular application.

Each of the electrodes 170 is electrically coupled to the implantable cochlear stimulator 150. Electronic circuitry within the implantable cochlear stimulator 150 may therefore be configured to apply stimulation current to selected pairs or groups of electrodes 170 in accordance with a specified stimulation pattern controlled by the sound processing unit 130.

As mentioned, the implantable cochlear stimulator 150 and lead 160 may be implanted within the patient while the sound processing unit 130 and the microphone 140 are configured to be located outside the patient, e.g., behind the ear. Hence, the implantable cochlear stimulator 150 and the sound processing unit 130 may be transcutaneously coupled via a suitable data or communications link 180. The communications link 180 allows power and control signals to be sent from the sound processing unit 130 to the implantable cochlear stimulator 150. In some embodiments, data and status signals may also be sent from the implantable cochlear stimulator 150 to the sound processing unit 130.

The external and implantable portions of the cochlear implant system 100 may each include one or more coils configured to transmit and receive power and/or control signals via the data link 180. For example, the external portion 110 of the cochlear implant system 100 may include an external coil 190 and the implantable portion of the cochlear implant system 120 may include an implantable coil 195. The external coil 190 and the implantable coil 195 may be inductively coupled to each other, thereby allowing data and power signals to be wirelessly transmitted between the external portion and the implantable portion of the cochlear implant system 100. Because in certain embodiments, the external portion 110 of the cochlear implant system 100 may not always be within close proximity to the implantable portion of the cochlear implant system 120, such as when the external portion 110 is removed for sleeping, the system may be configured to recognize when the implantable coil 195 and the external coil 190 are within range of one another.

Figure 2:
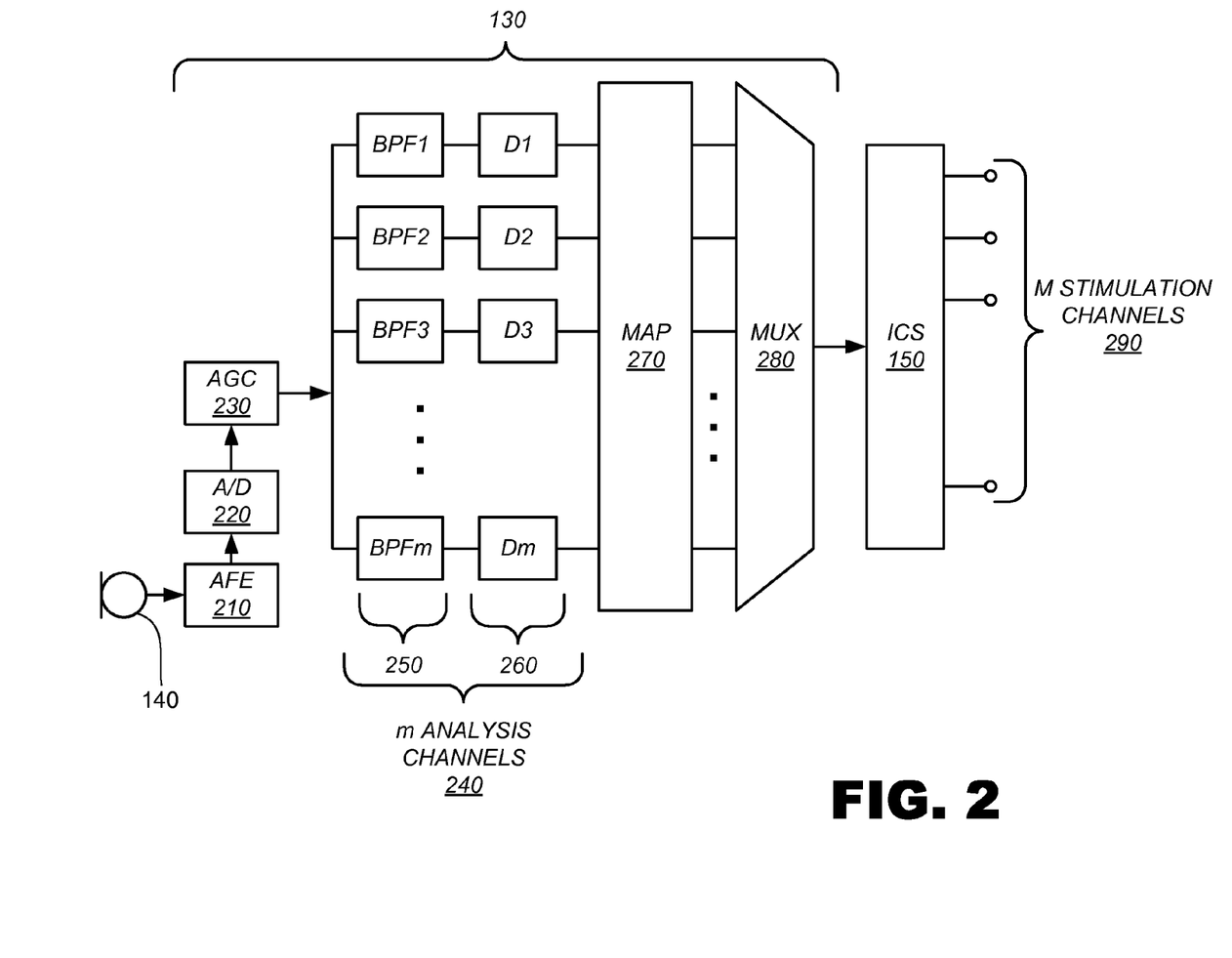
FIG. 2 is a functional block diagram of an exemplary sound processing unit and implantable cochlear stimulator according to principles described herein.

FIG. 2 is a functional block diagram of an exemplary sound processing unit 130 and implantable cochlear stimulator 150. The functions shown in FIG. 2 are merely representative of the many different functions that may be performed by the sound processing unit 130 and/or the implantable cochlear stimulator 150. A more complete description of the functional block diagram of the sound processing unit 130 and the implantable cochlear stimulator 150 is found in U.S. Pat. No. 6,219,580, which is incorporated herein by reference in its entirety.

As shown in FIG. 2, the microphone 140 senses acoustic information, such as speech and music, and converts the acoustic information into one or more electrical signals. These signals are then amplified in audio front-end (AFE) circuitry 210. The amplified audio signal is then converted to a digital signal by an analog-to-digital (A/D) converter 220. The resulting digital signal is then subjected to automatic gain control using a suitable automatic gain control (AGC) function 230.

After appropriate automatic gain control, the digital signal is then processed in one of a number of digital signal processing or analysis channels 240. For example, the sound processing unit 130 may include, but is not limited to, eight analysis channels 240. Each analysis channel 240 may respond to a different frequency content of the sensed acoustical signal. In other words, each analysis channel 240 includes a band-pass filter (BP1-BPFm) 250 or other type of filter such that the digital signal is divided into m analysis channels 240. The lowest frequency filter may be a low-pass filter, and the highest frequency filter may be a high-pass filter.

As shown in FIG. 2, each of the m analysis channels 240 may also include an energy detection stage (D1-Dm) 260. Each energy detection stage 260 may include any combination of circuitry configured to detect the amount of energy contained within each of the m analysis channels (240). For example, each energy detection stage 260 may include a rectification circuit followed by an integrator circuit. As will be described in more detail below, the cochlear implant system 100 may be configured to determine which of the m analysis channels 240 are presented to the patient via the stimulation channels 290 by analyzing the amount of energy contained in each of the m analysis channels 240.

After energy detection, the signals within each of the m analysis channels 240 are forwarded to a mapping stage 270. The mapping stage 270 is configured to map the signals in each of the m analysis channels 240 to one or more of M stimulation channels 290. In other words, the information contained in the m analysis channels 240 is used to define the stimulation current pulses that are applied to the patient by the implantable cochlear stimulator 150 via the M stimulation channels 290. As mentioned previously, pairs or groups of individual electrodes 170 make up the M stimulation channels.

In some examples, the mapped signals are serialized by a multiplexer 128 and transmitted to the implantable cochlear stimulator 150. The implantable cochlear stimulator 150 may then apply stimulation current via one or more of the M stimulation channels 290 to one or more stimulation sites within the patient's cochlea. As used herein and in the appended claims, the term "stimulation site" will be used to refer to a target area or location at which the stimulation current is applied. For example, a stimulation site may refer to a particular location within the neural tissue of the cochlea. Through appropriate weighting and sharing of currents between the electrodes 170, stimulation current may be applied to any stimulation site along the length of the lead 180.

Figure 3:
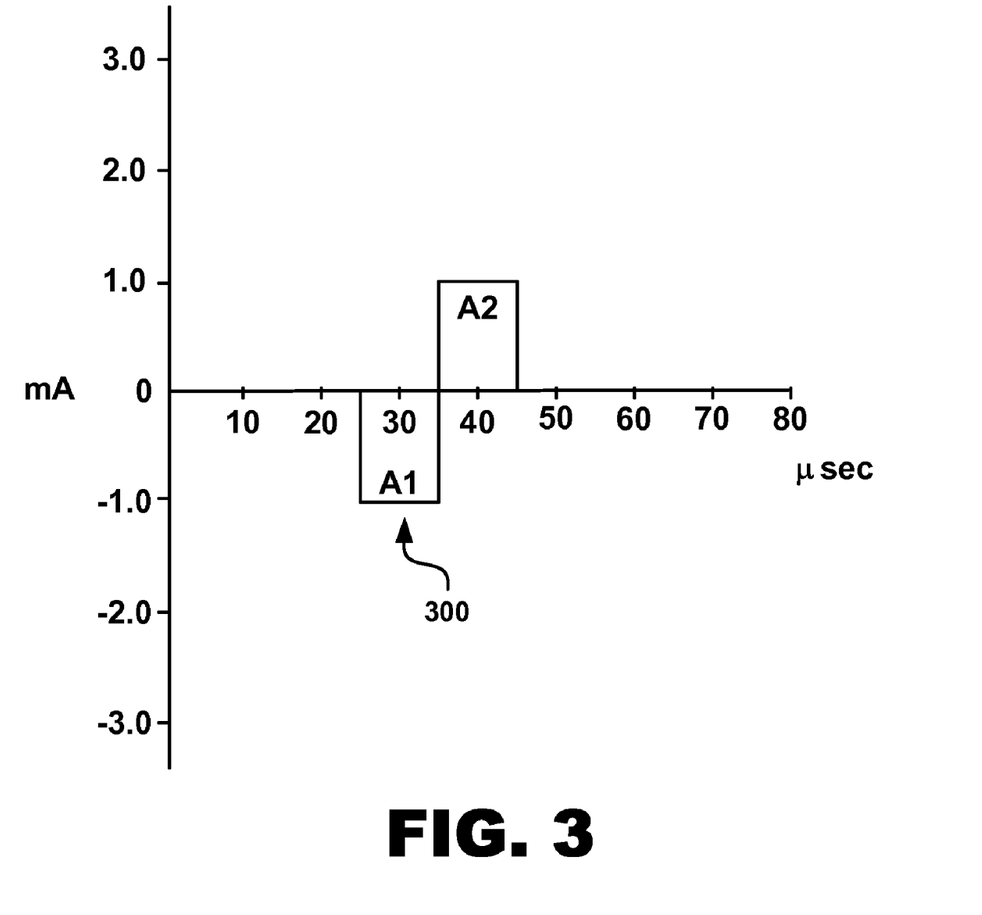
FIG. 3 illustrates an exemplary stimulation current pulse that may be delivered to neural tissue via one or more of stimulation channels according to principles described herein.

FIG. 3 illustrates an exemplary stimulation current pulse 130 that may be delivered to neural tissue via one or more of the stimulation channels 129. The stimulation current pulse 300 of FIG. 3 is biphasic. In other words, the pulse 300 includes two parts—a negative first phase having an area A1 and a positive second phase having an area A2. In some implementations, the negative phase A1 causes neural tissue to depolarize or fire. The biphasic stimulation pulse 300 shown in FIG. 3 has an amplitude of 1 milliamp (mA) and a pulse width of 20 microseconds (μ sec) for illustrative purposes only.

The combined areas of A1 and A2 are representative of a total amount of electric charge that is applied to a stimulation site by stimulation current pulse 300. The biphasic stimulation pulse 300 shown in FIG. 3 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulation pulse 300 may alternatively be charge-imbalanced as best serves a particular application.

In some examples, the total amount of charge per phase applied to a stimulation site within the cochlea by a stimulation current pulse 300 corresponds to a loudness level of an input audio signal as perceived by the patient. Hence, a change in the total amount of charge applied by a stimulation current pulse 300 may result in a change in the loudness level of an audio signal, which may affect the sound quality of the audio signal as perceived by the patient.

Figure 4:
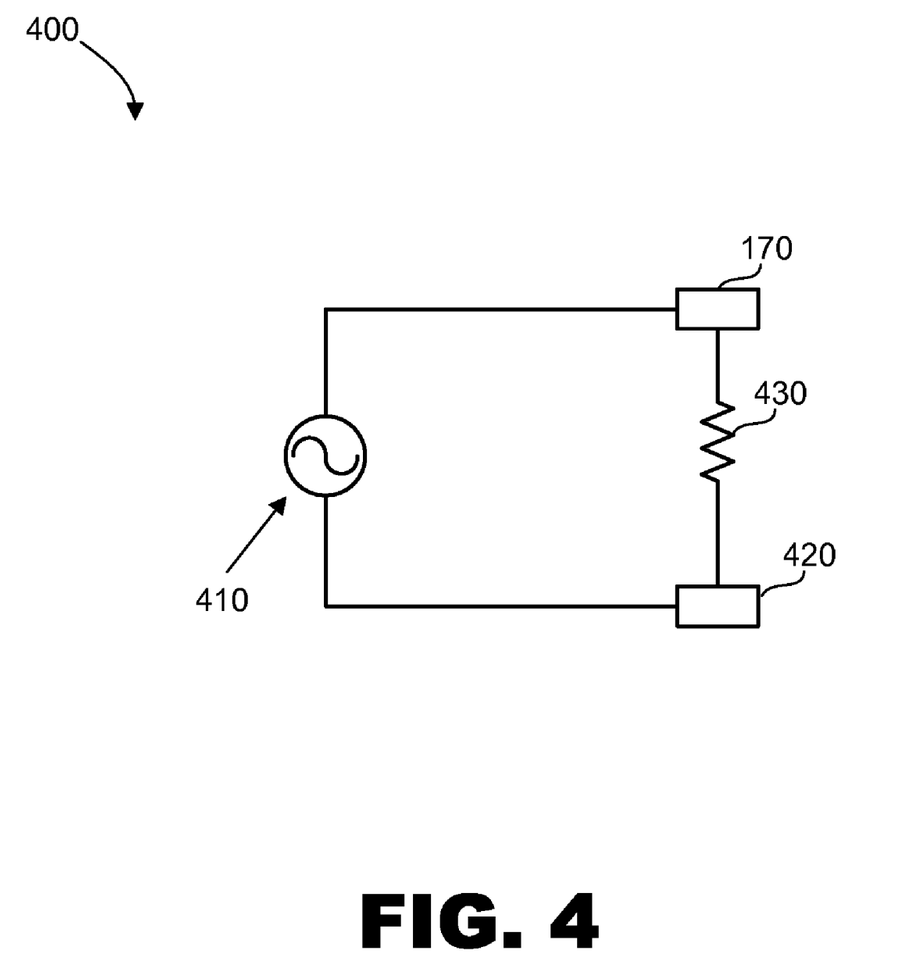
FIG. 4 illustrates an exemplary electrode configuration according to principles described herein.

One factor that may cause a change in the total charge per phase applied to a stimulation site is a change in electrode impedance. FIG. 4 will be used to illustrate the relationship between charge and electrode impedance.

FIG. 4 shows an exemplary circuit diagram 400 representative of a relationship between current applied to an electrode 170 and the impedance of the electrode 170. As shown in FIG. 4, the electrode 170 may be connected to a voltage source 410 configured to cause a current to be applied to the electrode 170. A return electrode 420 may also be included to complete the circuit. The return electrode 420 may include a ground, another one of the electrode 170, and/or the housing of the implantable cochlear stimulator 150. It will be assumed in the examples given herein that the return electrode 420 is ground.

As represented by resistor 430, an impedance may be associated with the electrode 170. The impedance may be dependent of the physiological properties of the tissue where the electrode 170 is implanted, the composition of the electrode 170 itself, and/or any other factor as may serve a particular application.

According to Ohm's law, the relationship between the voltage ("V") generated by voltage source 410, the current ("I") applied to the electrode 170, and the impedance ("Z") of the electrode 170 is V=I*Z. Thus, with a fixed maximum voltage, a change in impedance will cause an opposite change in the maximum current that may be applied to the electrode 170. For example, an increase in impedance would cause a decrease in maximum current, which in turn would cause a decrease in the total charge per phase applied to a stimulation site. This change in total charge applied to the stimulation site may have adverse effects on the loudness level or sound quality of an audio signal experienced by a patient.

A change in electrode impedance may be caused by many different factors. For example, changes in one or more physiological properties of tissue within the cochlea, aging, a change in body fat percentage, introduction of scar tissue, dehydration, and/or infection may lead to a change in electrode impedance. A change in electrode impedance may additionally or alternatively be caused by an electrode malfunction (e.g., an electrode may become shorted or open). A change in electrode impedance may be permanent in some instances (e.g., with aging) or temporary in others (e.g., during an infection).

As mentioned, a change in electrode impedance may result in a degradation of sound quality experienced by a patient. For example, a change in electrode impedance may result in a change in loudness level and/or distort pitch.

Such sound quality degradation may adversely affect the ability of the patient to recognize speech, music, and/or other sounds. This can be especially devastating for pediatric cochlear implant patients because the change in sound quality or volume may go unnoticed for long periods of time. Hence, an undetected change in electrode impedance can potentially interfere with the overall speech and language development of pediatric patients. It will be recognized that cochlear implant patients of all ages may experience similar difficulties if a change in electrode impedance is not detected and accounted for. As will be discussed in more detail below, a change in impedance may be compensated for by adjusting one or more of the stimulation parameters. In some examples, the adjustment of stimulation parameters may be configured to maintain constant a total charge per phase applied to a stimulation site within the cochlea.

Figure 5:
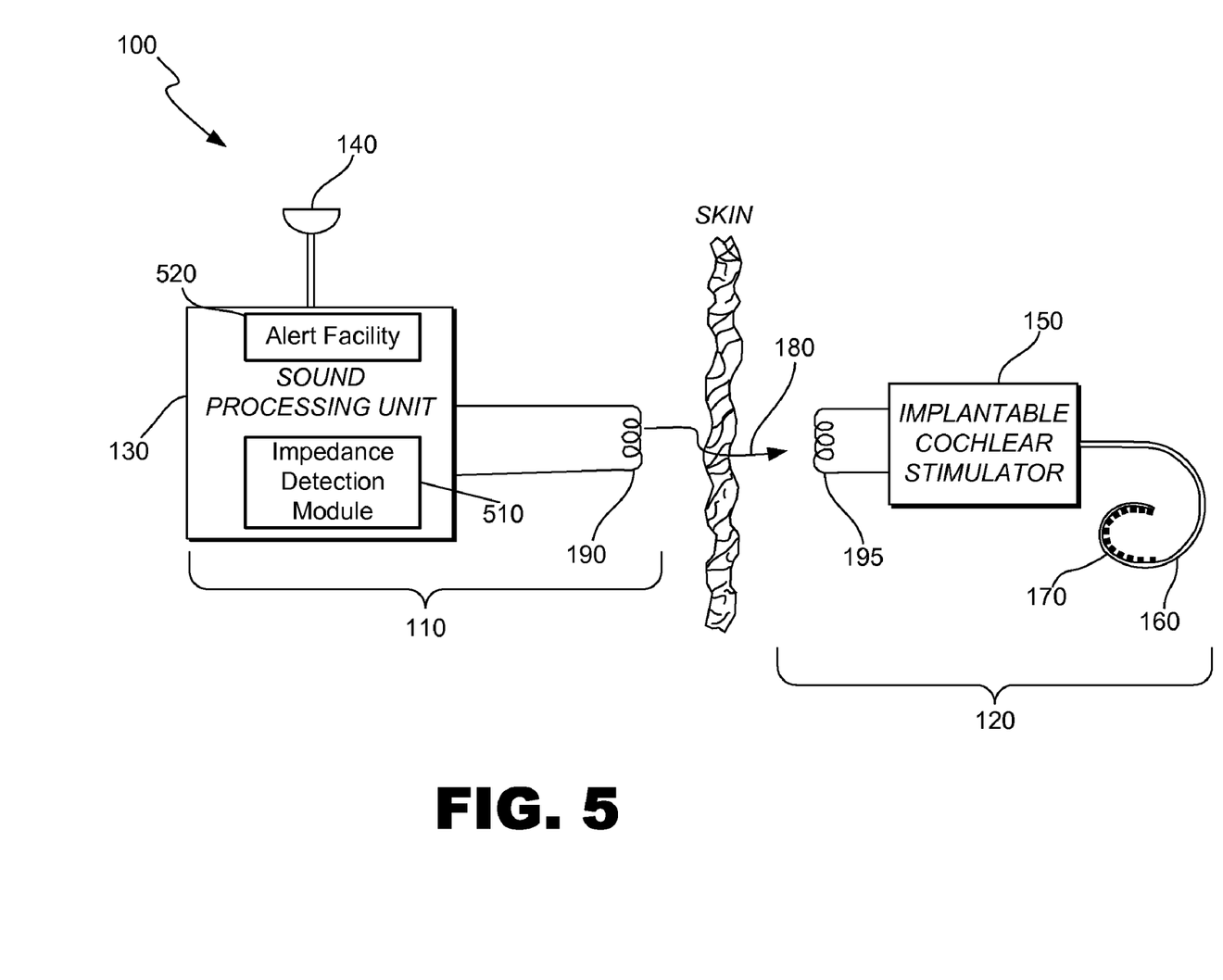
FIG. 5 illustrates an exemplary stimulation current pulse that may be delivered to neural tissue via one or more of stimulation channels according to principles described herein.

FIG. 5 depicts an exemplary cochlear implant system 100 configured to automatically detect an impedance of one or more electrodes 170 in accordance with a predefined schedule and perform one or more predefined actions accordingly in order to maintain an optimal perceived sound quality. As shown in FIG. 5, the sound processing unit 130 may include an impedance detection module 510 configured to automatically detect an impedance of one or more of the electrodes 170 in accordance with a predefined schedule. The impedance detection module 510 may include any combination of hardware, circuitry, and/or software configured to perform any of the functions described herein.

The impedance detection module 510 may be configured to detect one or more electrode impedances using any suitable technique. For example, the impedance detection module 510 may be configured to direct the implantable cochlear stimulator 150 to apply a current pulse having a known amplitude to each of the electrodes 170 and then measure the resulting voltages at each electrode 170. The impedance may then be determined by the impedance detection module 510 by dividing the measured voltage by the known current. It will be recognized that any other method of detecting electrode impedances may be used as may serve a particular application.

As mentioned, the impedance detection module 510 may be configured to automatically detect one or more electrode impedances according to a predefined schedule. In one particular embodiment, the impedance detection module 510 may be configured to automatically measure the impedances of the electrodes 170 each time the implantable coil 195 and the external coil 190 are brought within range of one another after having been separated. For example, the sound processing unit 130 is often removed from its operating location (e.g., behind the ear) to be recharged or otherwise serviced. Additionally or alternatively, the sound processing unit 130 may be removed from its operating location when the patient goes to bed or at other times as the patient may desire. When the patient places the sound processing unit 130 back in its operating position, the impedance detection module 510 may automatically measure one or more electrode impedances.

Additionally or alternatively, the impedance detection module 510 may be configured to periodically measure one or more electrode impedances. For example, the impedance detection module 510 may measure one or more electrode impedances every twelve or twenty-four hours. It will be recognized that any time period may be used as may serve a particular application.

The predefined schedule may be such that the impedance detection module 510 is configured to measure one or more electrode impedances in response to a sensed condition. For example, the implantable cochlear stimulator 150 may be configured to transmit data to the sound processing unit 130 representative of a status of operation of the implantable cochlear stimulator 150. The sound processing unit 130 may analyze this data and determine that it is abnormal in some way. The impedance detection module 510 may be directed to measure one or more electrode impedances in response to the detected abnormality in order to determine whether a change in impedance has caused the abnormality. In some alternative examples, one or more electrode impedances may be measured whenever the user connects the sound processing unit 130 to the implanted electrodes 170.

In some examples, the sound processing unit 130 may be configured to maintain a log of electrode impedance measurements. In this manner, a change in one or more of the electrode impedances may be detected. The log may be stored as log data within one or more data storage units that are a part of or in communication with the sound processing unit 130.

The sound processing unit 130 may be configured to perform one or more predefined actions in accordance with the detected electrode impedances. For example, if the sound processing unit 130 determines that a change in electrode impedance has occurred, the predefined action may include alerting the patient or the patient's caregiver of the change in electrode impedance through the use of an audible or visual alert. In one implementation, this alert can only be sounded if the change in impedance is deemed to cause an issue to quality of sound delivered to the patient. For example, if it is ascertained that the implanted electronics is not able to deliver required stimulation because of compliance limitations inherent in the device. In this manner, the patient or the patient's caregiver may be put on notice that the patient may need to visit a clinician to readjust the stimulation parameters accordingly.

To this end, the sound processing unit 130 may include an alert facility 520 configured to convey one or more alerts to the patient and/or other user. The alert facility 520 may include any combination of hardware, circuitry, and/or software as may serve a particular application. For example, the alert facility 520 may include one or more LEDs or graphical interfaces configured to display a visual alert representative of a detected change in electrode impedance. Additionally or alternatively, the alert facility 520 may include circuitry configured to generate an audible beep or other sound representative of a detected change in electrode impedance. It will be recognized that other types of alerts (e.g., vibrating alerts, text messages, emails, etc.) may be generated by the alert facility 520 and communicated to the patient and/or other person as may serve a particular application.

Another predefined action that may be performed by the sound processing unit 130 in response to a detected change in electrode impedance includes adjusting one or more stimulation parameters to compensate for the detected change in electrode impedance. For example, if an increase in impedance for a particular electrode 170 is detected, the sound processing unit 130 may be configured to adjust one or more stimulation parameters such that the total electric charge applied via the electrode 170 remains constant. These changes may be made in order to attempt to maintain a consistent loudness level as perceived by the patient.

To illustrate, a stimulation pulse applied to a particular electrode 170 may be similar to that shown previously in FIG. 3. After processing the data acquired by the impedance detection module 510, the sound processing unit 130 may determine that the impedance of the electrode 170 has doubled. This change in impedance may result in the amplitude of the current applied to the electrode 170 being reduced by one half to a value of 0.5 mA.

Figure 6:
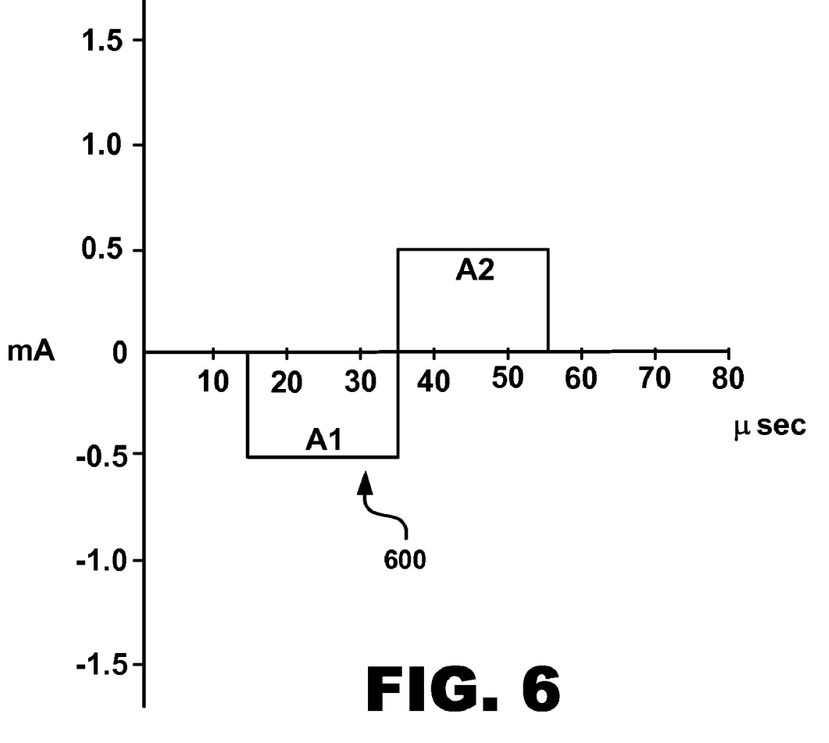
FIG. 6 illustrates an exemplary system configured to dynamically focus one or more excitation fields produced by current steering electrodes

FIG. 6 illustrates an exemplary stimulation current pulse 600 that may be delivered via the electrode 170 after the sound processing unit 130 has adjusted at least one stimulation parameter in response to the doubling in impedance of the electrode 170. As shown in FIG. 6, the pulse width of the stimulation current pulse 600 has been doubled compared to the pulse width of stimulation current pulse 300 shown in FIG. 3. In this manner, the total electric charge applied via the electrode 170 remains the same. It will be recognized that additional or alternative stimulation parameters governing the stimulation current applied via one or more electrodes 170 may be adjusted in response to a detected change in electrode impedance as may serve a particular application. Moreover, it will be recognized that the total charge per phase may be maintained constant using any other suitable method or technique.

Additional or alternative stimulation parameters may be adjusted to compensate for a detected change in electrode impedance. For example, a most comfortable stimulation level ("M level") and/or a quiet sound level ("T level") corresponding to electrical stimulation applied to a patient may be adjusted to compensate for a detected change in electrode impedance. Additionally or alternatively, values corresponding to a current amplitude versus pulse width curve may be stored in a look up table and used to determine an appropriate pulse width for a particular current amplitude caused by a change in impedance. These values may be obtained using any suitable heuristic and/or empirical data as may serve a particular application.

As mentioned, an electrode 170 that malfunctions or otherwise becomes disabled may result in a change in impedance of the electrode 170 and/or an abnormal impedance measurement. For example, an electrode 170 may become shorted or open. A shorted electrode 170 may have an impedance substantially equal to zero ohms. An open electrode 170 may have a relatively very large impedance value. Other electrode malfunctions may include, but are not limited to, partial shorting, irregular stimulation performance, etc. Such disabled electrodes may result in decreased sound quality and/or distorted pitch and may even render a cochlear implant system 100 useless to a patient.

In some examples, when the impedance detection module 510 detects an electrode impedance value indicative of a disabled electrode, the sound processing unit 130 may be configured to use current steering and/or other techniques to compensate for the disabled electrode.

Current steering may be used in configurations wherein a desired stimulation site corresponding to a disabled electrode 170 is located spatially in between two functioning electrodes 170. To effectively deliver stimulation to the stimulation site previously stimulated by the disabled electrode 170, weighted current may be applied simultaneously or in a time-interleaved manner via two or more electrodes 170 surrounding the disabled electrode 170. The basis for current steering is the phenomenon of summation of electrical fields, where the current delivered to the two electrodes sums together. A stimulation site located spatially in between the two electrodes 170 may be effectively stimulated due to the summation of electrical fields.

Figure 7:
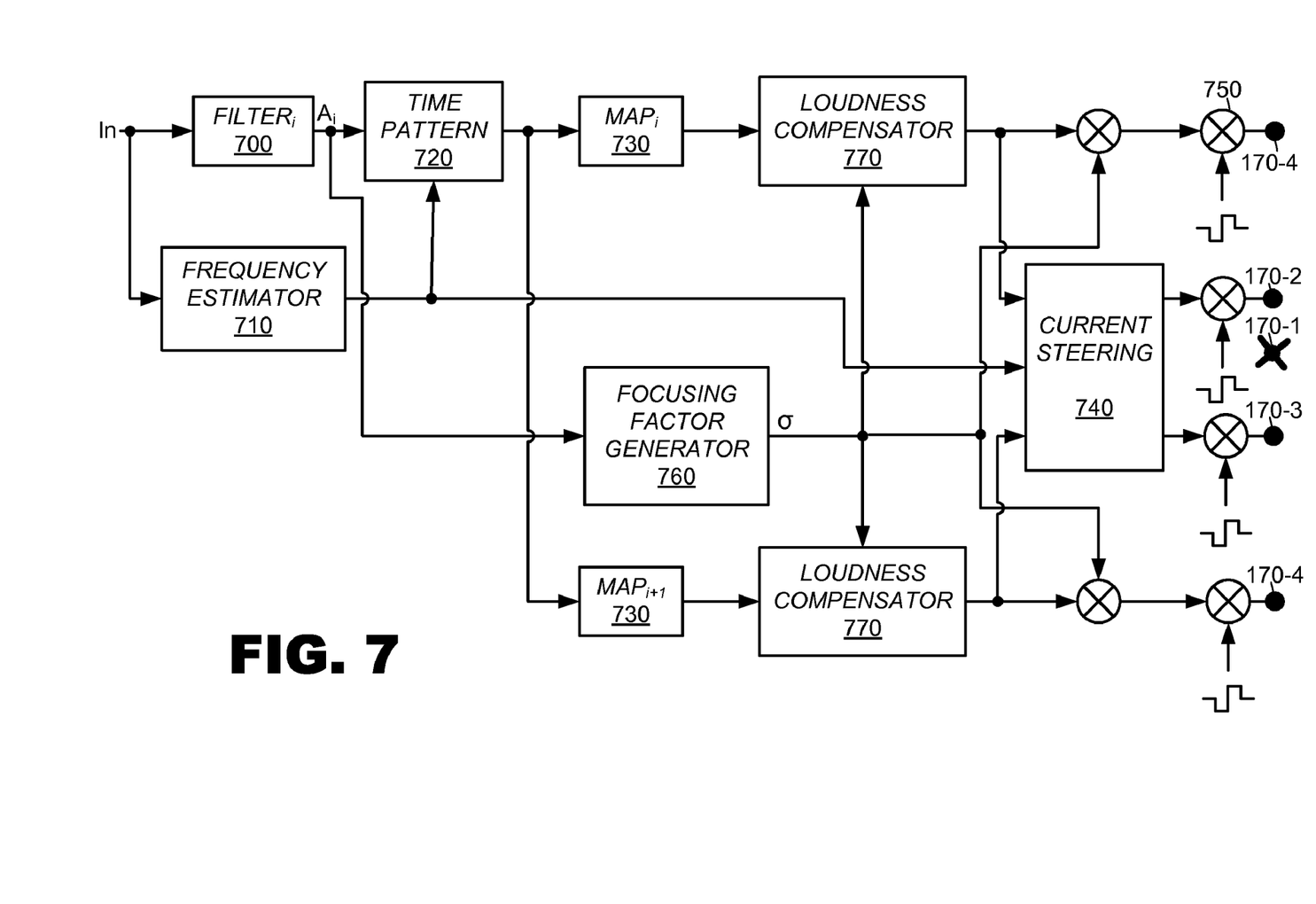
FIG. 7 is a diagram illustrating various possible stimulation sites in the tissue of a patient and illustrates the concept of current steering according to principles described herein.

Current steering will be further explained with reference to FIG. 7. FIG. 7 is a functional block diagram of an exemplary current steering strategy as applied via the cochlear implant system 100 of FIG. 5. The current steering strategy is configured to dynamically focus one or more excitation fields produced by current steering electrodes. It will be recognized that the strategy shown in FIG. 7 is merely exemplary and that it may include additional or alternative components and/or functions.

As shown in FIG. 7, a disabled electrode 170-1 may be surrounded by a plurality of properly functioning electrodes 170-2 through 170-5. All of the electrodes shown in FIG. 7 will be referred to herein collectively as "electrodes 170".

An input audio signal is filtered by one or more filters 700 configured to divide the signal into a number of frequency channels or bands. The input audio signal is also input into a frequency estimator 710 configured to estimate the peak frequency thereof. A time pattern block 720 is configured to build construct the temporal structure of a pulse train representing the signal output by the filter 700.

Mapping stages 730 are configured to map the amplitude of the signal output by the time pattern block 720 to corresponding current levels in accordance with a suitable mapping function.

The output of each mapping stage 730 is input into a current steering block 740. The current steering block 740 is also configured to receive the output of the frequency estimator 710. In some examples, the current steering block 740 is configured to determine appropriate weighting factors for current to be applied via at least two electrodes that surround the disabled electrode 170-1 (e.g., electrodes 170-2 and 170-3). This determination may be based at least in part on the peak frequency estimate and the output of each of the mapping functions 730. The weighting factors may be applied to the current using multiplication blocks 750. In this manner, stimulation current may be delivered to a stimulation site located in between the functioning electrodes 170-2 and 170-3.

The excitation field produced by electrodes 170-2 and 170-3 may be narrowed by applying compensating current simultaneously or in a time-interleaved manner via one or more additional electrodes (e.g., electrodes 170-4 and/or 170-5). A focusing factor generator 760 may be included and configured to generate the aforementioned focusing factor $\sigma$ based on the amplitude of the signal output by the filter 700. The focusing factor $\sigma$ is used to generate scaled versions of the current steering current. This scaled current is delivered via the one or more additional electrodes 170-4 and 170-5 to effectively narrow the excitation field produced by electrodes 170-2 and 170-3.

As shown in FIG. 7, loudness compensators 770 may also be included. The loudness compensators 770 are configured to adjust the amplitudes of the currents applied via electrodes 170-2 and 170-3 to compensate for loudness changes that may be caused by current delivered via the compensating electrodes 170-4 and 170-5.

Figure 8:
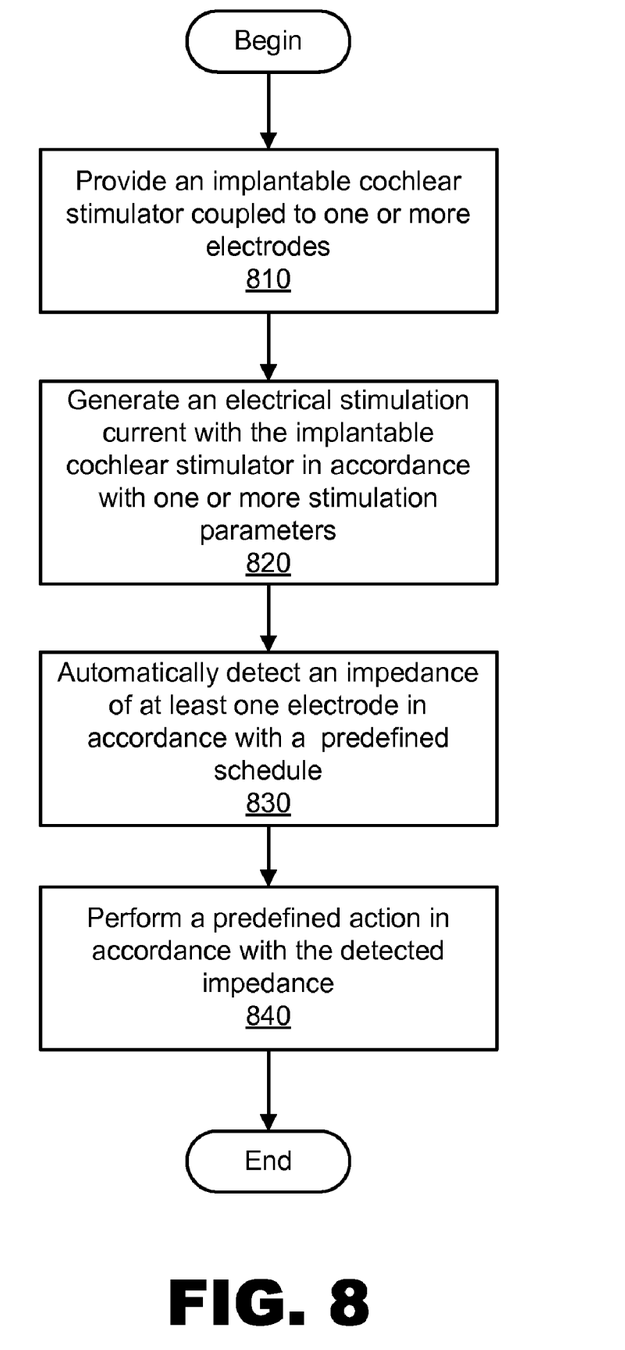
FIG. 8 is a block diagram that illustrates the main steps associated with a method according to principles described herein.

FIG. 8 illustrates an exemplary method of automatically detecting an impedance of one or more electrodes in a cochlear implant system. While FIG. 8 illustrates exemplary steps according to one embodiment, other embodiments may omit, add to, reorder, and/or modify any of the steps shown in FIG. 8.

In step 810, an implantable cochlear stimulator coupled to one or more electrodes is provided. The implantable cochlear stimulator may be similar to implantable cochlear stimulator 150, for example.

In step 820, an electrical stimulation current is generated with the implantable cochlear stimulator in accordance with one or more stimulation parameters. The stimulation current may be generated in any of the ways described herein.

In step 830, an impedance of at least one of the electrodes is automatically detected in accordance with a predefined schedule. The impedance of at least one of the electrodes may be detected in any of the ways described herein.

In step 840, a predefined action is performed in accordance with the detected impedance. The predefined action may include, but is not limited to, alerting the patient, a clinician, and/or other user, adjusting one or more stimulation parameters to compensate for a change in impedance, and/or maintaining constant a total electric charge applied via one or more electrodes as may serve a particular application.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
providing an implantable cochlear stimulator coupled to one or more electrodes;
generating an electrical stimulation current with said implantable cochlear stimulator in accordance with one or more stimulation parameters;
automatically detecting an impedance of at least one of said electrodes in accordance with a predefined schedule; and
adjusting, in accordance with said detected impedance, a pulse width of said electrical stimulation current to maintain constant a total electric charge level.

2. The method of claim 1, wherein said automatically detecting comprises periodically detecting said impedance of said at least one of said electrodes.

3. The method of claim 1, wherein said automatically detecting comprises detecting said impedance each time said implantable cochlear stimulator is connected to a sound processing unit.

4. The method of claim 1, further comprising adjusting, in accordance with said detected impedance, at least one of a total electric charge of said electrical stimulation current, a most comfortable current level, and a quiet sound level.

5. The method of claim 1, further comprising providing an alert if said detected impedance represents a change in impedance.

6. A method comprising:
providing an implantable cochlear stimulator coupled to one or more electrodes;
generating an electrical stimulation current with said implantable cochlear stimulator in accordance with one or more stimulation parameters;
automatically detecting an impedance of at least one of said electrodes in accordance with a predefined schedule;
using the detected impedance to identify at least one disabled electrode; and
using current steering to compensate for said disabled electrode.

7. The method of claim 6, further comprising using the detected impedance to identify at least one disabled electrode.

8. The method of claim 6, wherein said automatically detecting comprises periodically detecting said impedance of said at least one of said electrodes.

9. The method of claim 6, wherein said automatically detecting comprises detecting said impedance each time said implantable cochlear stimulator is connected to a sound processing unit.

10. A system comprising:
an implantable cochlear stimulator;
one or more electrodes electrically coupled to said implantable cochlear stimulator; and
a sound processing unit;
wherein said sound processing unit is configured to:
direct said implantable cochlear stimulator to apply an electrical stimulation current to a stimulation site within a patient via at least one of said electrodes;
automatically detect an impedance of at least one of said electrodes in accordance with a predefined schedule; and
adjust, in accordance with said detected impedance, a pulse width of said electrical stimulation current to maintain constant a total electric charge level.

11. The system of claim 10, wherein said sound processing unit is further configured to be selectively connected to said implantable cochlear stimulator and automatically detect said impedance upon connection of said sound processing unit to said implantable cochlear stimulator.

12. The system of claim 10, wherein said sound processing unit is configured to periodically detect said impedance.

13. A system comprising:
an implantable cochlear stimulator;
one or more electrodes electrically coupled to said implantable cochlear stimulator; and
a sound processing unit;
wherein said sound processing unit is configured to:
direct said implantable cochlear stimulator to apply an electrical stimulation current to a stimulation site within a patient via at least one of said electrodes;
automatically detect an impedance of at least one of said electrodes in accordance with a predefined schedule; and
maintain, in accordance with said detected impedance, a consistent loudness level of an audio signal as perceived by said patient.

14. A system comprising:
an implantable cochlear stimulator;
one or more electrodes electrically coupled to said implantable cochlear stimulator; and
a sound processing unit;
wherein said sound processing unit is configured to:
direct said implantable cochlear stimulator to apply an electrical stimulation current to a stimulation site within a patient via at least one of said electrodes;
automatically detect an impedance of at least one of said electrodes in accordance with a predefined schedule;
use the detected impedance to identify at least one disabled electrode; and
use current steering to compensate for said disabled electrode.

15. The system of claim 14, wherein said sound processing unit is further configured to provide an alert if said detected impedance represents a change in impedance.

16. A system comprising:
an implantable cochlear stimulator;
one or more electrodes electrically coupled to said implantable cochlear stimulator; and
a sound processing unit selectively and communicatively coupled to said implantable cochlear stimulator;
wherein said sound processing unit is configured to
direct said implantable cochlear stimulator to apply an electrical stimulation current to a stimulation site within a patient via at least one of said electrodes,
automatically detect an impedance of at least one of said electrodes in accordance with a predefined schedule, and
maintain a consistent sound quality of an audio signal as perceived by a patient.

17. The system of claim 16, wherein said sound processing unit is configured to periodically detect said impedance.

18. The system of claim 16, wherein said sound processing unit is further configured to be selectively connected to said implantable cochlear stimulator and automatically detect an impedance upon a connection of said sound processing unit to said implantable cochlear stimulator.

19. A method comprising:
providing an implantable cochlear stimulator coupled to one or more electrodes;
generating an electrical stimulation current with said implantable cochlear stimulator in accordance with one or more stimulation parameters;

automatically detecting an impedance of at least one of said electrodes in accordance with a predefined schedule; and maintaining, in accordance with said detected impedance, a consistent loudness level of an audio signal as perceived by said patient.

20. The method of claim 19, further comprising adjusting, in accordance with said detected impedance, a pulse width of said electrical stimulation current to maintain constant a total electric charge level.

* * * * *